United States Patent
Cheminal et al.

[11] Patent Number: 5,932,776
[45] Date of Patent: Aug. 3, 1999

[54] PROCESS FOR FLUORINATION OF PERCHLOROETHYLENE OR OF PENTACHLOROETHANE

[76] Inventors: Bernard Cheminal, "La Rivière" Orliènas, 69530 Brignais; Eric Lacroix, 52 Rue Laennec, 69008, Lyon; André Lantz, Domaine de la Hêtraie, 69390 Vernaison, all of France

[21] Appl. No.: 08/999,882

[22] Filed: Nov. 6, 1996

Related U.S. Application Data

[63] Continuation of application No. 08/492,312, Jun. 19, 1995, abandoned, which is a continuation of application No. 08/188,332, Jan. 26, 1994, abandoned.

[30] Foreign Application Priority Data

Jan. 27, 1993 [FR] France .................................. 93 00779

[51] Int. Cl.⁶ .................................................. C07C 17/08
[52] U.S. Cl. .......................................... 570/168; 570/169
[58] Field of Search ...................................... 570/168, 169

[56] References Cited

U.S. PATENT DOCUMENTS

| | | | |
|---|---|---|---|
| 2,435,551 | 2/1948 | Black | 260/449.6 |
| 2,900,423 | 8/1959 | Smith | 502/315 X |
| 3,650,987 | 3/1972 | Veechio et al. | 570/168 |
| 3,661,805 | 5/1972 | Horvath | 502/315 |
| 3,787,331 | 1/1974 | Gioppelli et al. | 570/168 |
| 3,793,229 | 2/1974 | Groppelli et al. | 570/168 |
| 3,804,778 | 4/1974 | Ramanadin | 502/228 |
| 4,131,616 | 12/1978 | Stiles | 260/449.6 |
| 4,439,534 | 3/1984 | Foulletier | 502/8 |
| 4,748,285 | 5/1988 | Foulletier | 570/169 |
| 4,766,280 | 8/1988 | Manzer et al. | 510/168 |
| 4,912,270 | 3/1990 | Carlson et al. | 570/169 |

FOREIGN PATENT DOCUMENTS

| | | |
|---|---|---|
| 37179/89 | 6/1989 | Australia . |
| 27038/92 | 10/1992 | Australia . |
| 0 055 652 | 7/1982 | European Pat. Off. . |
| 0 128 510 | 12/1984 | European Pat. Off. . |
| 2 276 098 | 1/1976 | France . |
| 2407021 | 5/1979 | France . |
| 2178237 | 7/1990 | Japan . |

*Primary Examiner*—Alan Siegel

[57] ABSTRACT

The invention relates to catalytic fluorination of perchloroethylene or of pentachloroethane in the gas phase by means of hydrofluoric acid.

A mixed catalyst is employed, made up of nickel and chromium oxides, halides and/or oxyhalides deposited on a support consisting of aluminium fluoride or of a mixture of aluminium fluoride and alumina.

16 Claims, No Drawings

PROCESS FOR FLUORINATION OF PERCHLOROETHYLENE OR OF PENTACHLOROETHANE

This is a continuation of application Ser. No. 08/492.312, filed on Jun. 19, 1995, now abandoned which is a continuation of application Ser. No. 08/188,332 filed Jan. 26, 1994, abandoned.

FIELD OF THE INVENTION

The present invention relates to a continuous process for fluorination of perchloroethylene or of pentachloroethane and its subject is more-particularly the fluorination of these compounds in the gas phase by means of hydrofluoric acid in the presence of a catalyst.

BACKGROUND OF THE INVENTION

The desired compounds (referred to as a group hereinafter by the expression "F120 series") are: F121 ($CHCl_2$—$CCl_2F$), F122 ($CHCl_2$—$CClF_2$), F123 ($CHCl_2$—$CF_3$), F124 ($CHClF$—$CF_3$), F125 ($CHF_2$—$CF_3$) or their isomers which can be employed either as substituents for perfluorocarbons (C.F.C.) in the fields of foams (blowing agents and insulants), aerosols (propellent agents) or in refrigeration, or else as intermediates for the synthesis of these substitutes. Efficient processes for their industrial production, and more particularly for that of F124 and of F125 are sought after at present.

Patent FR 1,315,351 describes a gas phase process for fluorination of haloolefins with a catalyst prepared by partial fluorination of an alumina impregnated with one or a number of halides of polyvalent metals such as chromium, nickel, cobalt, manganese etc. The authors stress the partial fluorination of the catalyst because it turns out, in their case, that an advanced (>80%) fluorination of the said catalyst results in a rapid loss of activity. The tests of Example 4 describing the fluorination of perchloroethylene are carried out with a catalyst based on chromium and cobalt derivatives deposited on $Al_2O_3$. At low temperature (T<290° C.), despite an $HF/C_2Cl_4$ molar ratio of 5, the inventors obtained a mixture of F121, F122, F123 and of the olefins F1111 ($CFCl$=$CCl_2$) and F1112a ($CF_2$=$CCl_2$). In the case of this mixture it is noted that F123 is clearly predominant but apparently the authors do not observe the formation of F124, F124a ($CF_2Cl$—$CHF_2$) and F125. Furthermore, it is concluded that the selectivities for olefins are high already at low temperature and increase with the latter.

Patent Application WO 8911467 claims the preparation of F123 and/or of F124 by gas phase fluorination of perchloroethylene using HF in the presence of a catalyst comprising a metal—in an oxidation state higher than zero—chosen from the group consisting of Cr, Co, Mn, Rh and Ni on an alumina support, highly fluorinated. In contrast to the preceding patent it appears necessary to fluorinate the catalyst strongly ($AlF_3$>90%) before going on to fluorinate the organic products. The object of the process claimed is to produce F123 and F124 while minimizing the formation of F125. The authors' preferred metal is cobalt; however, according to the examples, it is found that, whatever the metal tested: Cr, Co, Mn or Ni, and despite high temperatures and $HF/C_2Cl_4$ molar ratios, the selectivities for F125 remain very low (<10 %). Furthermore, numerous byproducts (outside the F120 series) are formed; in particular, with chromium or nickel the selectivities for F123+F124+F125 do not exceed 85–87% when operating at 350° C.

Patent Application JP 2-178237 describes the gas phase fluorination of perchloroethylene on bulk catalysts consisting of chromium oxides and of at least one of the following metals: Al, Mg, Ca, Ba, Sr, Fe, Ni, Co and Mn. Despite quite high temperatures (350–380° C.), the bulk catalysts exemplified (cometal Al, Mg, Ca, Ba, Sr or Fe) result in high selectivities for F122, whereas those for F125 remain lower than 15%. Now, as indicated in Patent Application FR 2,661,906, F122 is not an intermediate of great interest for the synthesis of F123–F124–F125 because it gives rise to numerous byproducts, especially olefins.

Patent Application EP 366 797 claims a process for fluorination of saturated or unsaturated compounds in the presence of catalyst based on porous and very pure alumina (containing less than 100 ppm of sodium), used as support for metal fluorides (nickel, cobalt, iron, chromium, manganese, copper or silver). This technique, which requires a catalyst of high purity, is illustrated in the case of the F120 series (pentahaloethanes) by two examples (27 and 30) with a chromium-based catalyst supported on alumina. In one case F123 is obtained predominantly, but in low yields (20%), by gas phase fluorination of $C_2Cl_4$; in the other case, depending on the reaction temperature, it is F124 or F125 that predominates, but this time the underlying reaction is fluorination (addition of HF and then Cl/F exchange) of F1113 ($CClF$=$CF_2$).

Patent Application FR 2,661,906 relates to the synthesis of F124 and of F125 by gas phase fluorination of F123 with a chromium-based catalyst deposited on active carbon. On catalysts of this type F123 gives rise to few byproducts that cannot be turned to profit, such as the compounds F115 ($CF_3$—$CF_2Cl$), F114a ($CF_3$—$CFCl_2$), F114 ($CF_2Cl$—$CF_2Cl$) and F133a ($CF_3$—$CH_2Cl$) or that can be detrimental to the catalyst life, such as the olefin F1111. On the other hand, it is indicated in this same patent that the underfluorinated compounds of F123 (F122, F121, $C_2Cl_4$ etc.) are not good precursors for F124 and F125.

This finding is confirmed by U.S. Pat. No. 3,258,500, which claims the use of chromium, bulk or supported on alumina, for gas phase fluorination reactions. Thus, Example 17 (column 14) describes the fluorination of perchloroethylene at 400° C. with an $HF/C_2Cl_4$ molar ratio of 6.2/1; in this case the selectivity for F123+F124+F125 is low (47.7%). A decrease in the reaction temperature (300° C.) changes this F123+F124+F125 selectivity only to 79.7% and in this case F125 is no longer the predominant compound.

Patent Application FR 2,669,022 describes the use of a catalyst based on nickel and chromium which are supported on $AlF_3$ or fluorinated alumina for the specific fluorination of F133a ($CF_3$—$CH_2Cl$) to F134a ($CF_3$—$CH_2F$), this catalyst enabling very good selectivities for F134a to be obtained.

DESCRIPTION OF THE INVENTION

It has now been found that this type of catalyst is very suitable for the preparation of compounds of the F120 series and more particularly that of the compounds F123, F124 and F125 from perchloroethylene or pentachloroethane. With this catalyst it is possible, in fact, to obtain a very high degree of conversion of the starting compound (95% or more) and at the same time an excellent total selectivity for F123+F124+F125 (of the order of 90% or more).

The subject of the invention is therefore a continuous process for catalytic fluorination of perchloroethylene or of pentachloroethane in the gas phase, by means of hydrofluoric acid, characterized in that a mixed catalyst is employed, made up of nickel and chromium oxides, halides and/or oxyhalides deposited on a support consisting of aluminium fluoride or of a mixture of aluminium fluoride and alumina.

This catalyst can be prepared in a manner known per se from an activated alumina. In a first stage the latter may be converted to aluminum fluoride or a mixture of aluminium fluoride and alumina by fluorination with the aid of air (or of an inert substance such as nitrogen) and hydrofluoric acid, the degree of conversion of alumina to aluminium fluoride depending essentially on the temperature at which the fluorination of alumina is performed (generally between 200 and 450° C., preferably between 250 and 400° C.). The support is next impregnated with the aid of aqueous solutions of chromium and nickel salts or with the aid of aqueous solutions of chromic acid, of nickel salt and of a chromium reducer such as methanol.

When chromic acid ($CrO_3$) is employed as chromium precursor this chromium can be reduced by any means known to a person skilled in the art (chemical reducing agent, thermal reduction etc.), provided that the technique employed does not impair the catalyst's properties and hence its activity. The preferred chemical reducing agent is methanol.

It is preferable to employ chlorides as chromium and nickel salts, but it is also possible to employ other salts such as, for example, oxalates, formates, acetates, nitrates and sulphates or nickel dichromate, provided that these salts are soluble in the quantity of water capable of being absorbed by the support.

The catalyst employed in the process according to the invention can also be prepared by direct impregnation of alumina with solutions of the abovementioned chromium and nickel compounds. In this case the conversion of at least a proportion (70% or more) of the alumina to aluminium fluoride is performed during the catalyst activation stage.

The activated aluminas to be employed for the preparation of the catalyst according to the present invention are well-known products which are available commercially. They are generally prepared by calcining alumina hydrates at a temperature of between 300 and 800° C. The activated aluminas which can be employed within the scope of the present invention may have high sodium contents (up to 1000 ppm) without this being detrimental to the catalytic activity.

The catalyst according to the invention may contain, on a mass basis, from 0.5 to 20% of chromium and from 0.5 to 20% of nickel and, preferably between 2 and 10% of each of the metals in a nickel/chromium atomic ratio of between 0.5 and 5, preferably close to 1.

Before being capable of catalysing the reaction of fluorination of perchloroethylene or of pentachloroethane, the catalyst according to the invention must be conditioned, that is to say converted into constituents that are active and stable (under reaction conditions) by a preliminary so-called activation operation.

This treatment may be carried out either in situ (in the fluorination reactor) or else in a suitable apparatus designed to withstand the conditions of activation. The latter generally comprises the following stages:

drying at low temperature (100 to 150° C., preferably 110 to 130° C.) in the presence of air or nitrogen, drying at high temperature (250 to 450° C., preferably 300 to 350° C.) under nitrogen or under air, low-temperature fluorination (180 to 300° C., preferably at approximately 200° C.) by means of a mixture of hydrofluoric acid and nitrogen, the HF content being controlled so that the temperature does not exceed 300° C., and finishing under a stream of pure or nitrogen-diluted hydrofluoric acid at a temperature which may range up to 450° C.

During this operation the catalyst precursors (nickel and chromium halides, nickel chromate and dichromate, chromium oxide) are converted into the corresponding fluorides and/or oxyfluorides, resulting in a release of water and/or hydrochloric acid.

This activation also contributes to increasing the fluorination of the alumina when the impregnation has been carried out on an already partially fluorinated support or, when alumina is impregnated directly, to the fluorination of the latter. In this latter case the temperature must be controlled perfectly (fluorination of alumina is highly exothermic) if the physical characteristics of the catalyst are not to be impaired; furthermore, the quantities of water which are generated are markedly greater.

After activation the inorganic composition of the catalyst according to the invention can be verified by a chemical analysis of the elements (chromium, nickel, fluorine, aluminium, oxygen).

The operating conditions for the synthesis of fluorinated compounds of the F120 series by gas phase fluorination of perchloroethylene or of pentachloroethane with the aid of hydrofluoric acid in the presence of the catalyst according to the invention are the following:

a) The reaction temperature is generally between 200 and 450° C. and depends on the final product sought after. F125 requires higher temperatures than F124 (and itself higher than F123). The optimum temperature is between 250 and 400° C.

b) The contact time, calculated as being the time for the gases (under the reaction conditions) to pass through the volume of catalyst in bulk, is between 3 and 100 seconds and more particularly between 5 and 30 seconds. However, in order to obtain a good compromise between the degree of conversion of the starting material and high production efficiencies of final products, the best range is from 7 to 20 seconds.

c) The $HF/C_2Cl_4$ (or $C_2HCl_5$) molar ratio may range from 1/1 to 20/1 and preferably from 2/1 to 10/1. Here, too the degree of conversion of the starting organic compound and the distribution of the products formed within the F120 series depend on the molar ratio chosen, an increase in this molar ratio resulting in an improvement in the overall degree of conversion and in a shift of the products formed towards more highly fluorinated compounds (F124 and F125). It must be noted, however, that too low a molar ratio (lower than stoichiometry) increases the formation of nonrecyclable products (perhaloethanes, tetrahaloethanes and olefins), it being possible for the latter to impair the stability of the catalyst activity.

d) Compounds of the F120 series which are underfluorinated (in relation to the desired product) can be recycled to the reactor. However, too high proportions of some of them (especially F122 and F121) in the reactor feed can give rise to a deactivation of the catalyst by fouling through the formation of olefins (F1111, F1112a etc.).

e) Under operating conditions which are capable of fouling the catalyst it may be judicious to introduce a low concentration of oxygen with the reactants. Depending on the operating conditions this concentration may vary between 0.02 and 5% in the relation to the organic reactants (molar percentage). This oxidant is intended to react with the "heavies" which cause the catalyst fouling.

f) The reaction according to the invention may be conducted at atmospheric pressure or at a pressure which is higher than the latter. For practical reasons the operation will be generally carried out in a region ranging from 0 to 25 bars gauge.

g) The catalyst can operate either in a fluidized bed or in a stationary bed. When the starting organic compound is perchloroethylene it is preferable—in order easily to remove the heat generated by the addition of HF to the double bond—to work in a fluid bed, in a tubular reactor or in a stationary bed with a high recycle ratio of stable compounds of the F120 series, whose fluorination is not very exothermic (F123, F124 etc.).

h) When the products sought after are highly fluorinated compounds like F124 or F125, dividing the reaction into two stages (two reactors) may be envisaged.

i) The material employed for constructing the plant must be compatible with the presence of hydrogen acids such as HCl and HeF; it may be chosen from "Hastelloy" or "Inconel", which withstand the corrosive mixtures containing these hydrogen acids.

The application of the process according to the invention makes it possible to obtain compounds of the F120 series with very good selectivities for the products sought after and/or for products which can be recycled. In fact, the type of catalyst proposed allows access to these compounds of the F120 series while limiting the formation of products that cannot be turned to profit, like perhaloethanes and tetrahaloethanes, or the formation of olefins which result from a dehydrohalogenation of the compounds of the F120 series and foul the catalyst. Limitation of the former ones makes it possible to improve the plant profitability; that of the latter acts upon the catalyst life and on the addition of oxygen. It should be noted that while this oxidant has a beneficial effect on the catalyst fouling, it may play a detrimental part by increasing the formation of perhalogenated compounds which cannot be turned to profit, via the Deacon reaction. Now, despite the presence of chromium in the catalyst (cf. Chemical Week 1987, 24 Jun., page 18), it has been found that the combined use of chromium and nickel directs the consumption of this oxidizing agent—when present—preferentially towards the oxidation of the "heavies" and therefore limits the Deacon reaction and thereby the formation of perhaloethanes which cannot be turned to profit and which can only interfere with the purification of the good products (the case of F115 in relation to F125).

Finally, the catalyst according to the invention makes it possible to obtain directly from perchloroethylene or pentachloroethane, in a single pass and with output efficiencies compatible with industrial production ($HF/C_2Cl_4$ or $C_2HCl_5$ molar ratio lower than 10; contact time shorter than 20 s) high selectivities for highly fluorinated compounds of the F120 series (F124, F125) (of the order of 25 to 40% in the case of each product) this being with few products that cannot be turned to profit (<10%).

EXAMPLES

The following examples illustrate the invention without limiting it.

Example 1

1A—CATALYST PREPARATION AND ACTIVATION 250 ml of a support containing, by weight, 73% of aluminium fluoride and 27% of alumina, obtained in a preceding stage by fluorination of Grace HSA alumina in a fluidized bed at about 300° C. with the aid of air and hydrofluoric acid (volume concentration of 5 to 10% of this acid in air) were placed in a rotary evaporator. The starting Grace HSA alumina had the following physicochemical characteristics:

form: beads 1–2 mm in diameter

BET surface: 220 $m^2/g$ pore volume: 1.2 $cm^2/g$ (in the case of pore radii of between 4 nm and 63 $\mu m$)

sodium content: 600 ppm.

Two separate aqueous solutions were also prepared:

(a) chromic solution with the addition of nickel chloride, containing:

chromic anhydride 12.5 g nickel chloride hexahydrate : 29 g water : 42 g (b) methanolic solution containing:

methanol : 18 g water : 50 g.

The mixture of these two solutions was then introduced, at ambient temperature at atmospheric pressure and over approximately 45 minutes, onto the stirred support. The catalyst was then dried under a stream of nitrogen, in a fluidized bed, at about 110° C. for 4 hours.

100 ml (77.5 g) of dry catalyst were charged into a tubular reactor made of Inconel with an internal diameter of 27 mm and the temperature was raised to 120° C. under a stream of nitrogen at atmospheric pressure. This treatment was maintained for about ten hours and the nitrogen was then gradually replaced with hydrofluoric acid, care being taken that the temperature increase did not exceed 95° C. and, when an $HF/N_2$ molar ratio of 50/50 was reached, the temperature was raised to 300° C.

After disappearance of the exothermicity peaks, the temperature was raised to 350° C. under a stream of pure hydrofluoric acid (1 mole/hour) for 6 hours.

The catalyst was finally purged under a stream of nitrogen before commencing the catalyst test. The characteristics of the catalyst A thus dried and activated were the following:

chemical composition (by weight)

fluorine : 64.4% aluminium : 27.2% nickel : 3.75% chromium : 3.3% oxygen : 1.35% physical properties:

BET surface : 35.4 $m^2/g$ volume of pores with a radius of between 4 nm and 63 $\mu m$ : 0.47 $cm^3/g$ surface area of the pores with a radius greater than 4 nm : 32.8 $m^2/g$.

1B—FLUORINATION OF PERCHLOROETHYLENE

The performance of catalyst A in the fluorination of perchloroethylene was tested at atmospheric pressure, without oxygen addition, under the operating conditions and with the results collated in Table 1 which follows.

TABLE 1

| TEST No. | 11 | 12 |
|---|---|---|
| Operating conditions: | | |
| - Temperature (°C.) | 350 | 300 |
| - HF/C$_2$Cl$_4$ molar ratio | 6.8 | 7.0 |
| - Contact time (s) | 15.9 | 16.7 |
| - Catalyst age (h) | 24 | 48 |
| Results: | | |
| - Overall degree of conversion of C$_2$Cl$_4$ (%) | 96.0 | 98.3 |
| - Selectivity (mol %) for: | | |
| F125 | 23.4 | 1.9 |
| F124 | 32.9 | 27.1 |
| F124a | 0.4 | 0.6 |
| F123 | 38.9 | 68.7 |
| F123a | 0.2 | 0.2 |
| F122 | 0.2 | 0.4 |
| F121 | 0 | 0 |
| F133a | 1.3 | 0.3 |
| F115 | 1.0 | 0.1 |
| F114 + F114a | 0.7 | 0.3 |
| F1111 | 0.7 | 0.3 |

Example 2

A catalyst B according to the invention was prepared, in which the chromium and nickel contents were substantially twice those of catalyst A. The operation was carried out as in Example 1A but using the following two aqueous solutions:

(a) Chromic solution with the addition of nickel chloride, containing
   chromic anhydride : 25 g
   nickel chloride hexahydrate : 58 g
   water : 40 g
(b) Methanolic solution containing:
   methanol : 35 g
   water : 30 g.

After drying and activation the characteristics of catalyst B were the following:
   chemical composition (by weight)
      fluorine : 58.5%
      aluminium : 25.1%
      nickel : 6.8%
      chromium : 5.6%
   physical properties:
      BET surface : 15.1 m$^2$/g
      volume of pores with a radius of between 4 nm and 63 μm : 0.382 cm$^3$/g
      surface area of the pores with a radius greater than 4 nm : 18 m$^2$/g.

Table 2, which follows, collates the operating conditions and the results obtained with this catalyst B in the fluorination of perchloroethylene at atmospheric pressure.

TABLE 2

| TEST No. | 21 | 22 | 23 | 24 |
|---|---|---|---|---|
| Operating conditions: | | | | |
| - Temperature (°C.) | 50 | 350 | 330 | 300 |
| - HF/C$_2$Cl$_4$ molar ratio | 7.4 | 7.2 | 7.2 | 7.3 |
| - Contact time (s) | 15 | 15.5 | 16.5 | 16.8 |
| - Catalyst age (h) | 44 | 556 | 315 | 453 |
| Results: | | | | |
| - Overall degree of conversion of C$_2$Cl$_4$ (%) | 95.6 | 94.6 | 95 | 94.1 |
| - Selectivity (mol %) for: | | | | |
| F125 | 32 | 34.1 | 25.5 | 8.3 |
| F124 | 28.4 | 24.2 | 31.3 | 33.5 |
| F124a | 0.4 | 0.3 | 0.3 | 0.6 |
| F123 | 33.3 | 33.1 | 39.3 | 54.6 |
| F123a | 0.2 | 0.3 | 0.2 | 0.4 |
| F122 | 0.2 | 0.3 | 0.3 | 0.6 |
| F121 | traces | 0 | 0 | 0 |
| F133a | 1.6 | 2.5 | 0.9 | 0.5 |
| F115 | 1.3 | 1.4 | 0.4 | 0.005 |
| F114 + F114a | 1.2 | 2.2 | 0.8 | 0.5 |
| F1111 | 1.0 | 1.4 | 0.9 | 0.9 |

Examples 3 to 5 (comparative)

By way of comparison, three catalysts C, D and E not in accordance with the present invention were prepared as follows:

Ex.3: Catalyst C without chromium

The operation was carried out as in Example 1A but leaving out the methanolic solution (b) and replacing the chromic solution (a) with a solution of 59 g of nickel chloride hexahydrate in 75 g of water.

Ex.4: Catalyst D without nickel

The operation was carried out as in Example 1A but replacing solution (a) with a solution of 25 g of chromic anhydride in 54 g of water.

Ex.5: Catalyst E (Ni+Cr on carbon)

250 ml of a vegetable active carbon support, dried beforehand at 150° C., which exhibits the following physicochemical characteristics were placed in a rotary evaporator:
   apparent density : 0.41
   particle size : 0.8 mm extrudates
   BET surface : 922 m$^2$/g
   surface area of the pores from 5 to 25 nm : 20.4 m$^2$/g
   surface area of the pores from 25 to 32 nm : 3.2 m$^2$/g
and were impregnated with an aqueous solution containing 13 g of chromic anhydride, 29 g of nickel chloride hexahydrate and 62 g of water.

The catalyst was next dried under a stream of nitrogen, in a fluidized bed, at about 110° C. for 4 hours.

100 ml (50.4 g) of dry catalyst were charged into a tubular reactor and an activation identical with that of Example 1A was carried out. The characteristics of the catalyst thus dried and activated were the following:
   chemical composition (by weight)
      fluorine : 12.9%
      nickel : 7.4%
      chromium : 5.2%
   physical properties:
      BET surface : 572 m$^2$/g
      volume of pores with a radius of between 4 nm and 63 μm : 0.52 cm$^3$/g
      surface area of the pores with a radius greater than 4 nm : 28.5 m$^2$/g.

Table 3, which follows, collates the operating conditions and the results obtained with the comparative catalysts C, D and E in the fluorination of perchloroethylene at atmospheric pressure.

TABLE 3

| EXAMPLE | 3 | 4 | | | 5 | |
|---|---|---|---|---|---|---|
| Operating conditions: | | | | | | |
| - Catalyst | C | D | D | D | E | E |
| - Temperature (°C.) | 350 | 350 | 300 | 300 | 350 | 320 |
| - HF/$C_2Cl_4$ molar ratio | 6.8 | 7.3 | 7.5 | 7.2 | 6.9 | 8.3 |
| - Contact time (s) | 15.9 | 14.9 | 14.0 | 14.7 | 15.6 | 16.9 |
| - Catalyst age (h) | 43 | 48 | 291 | 434 | 24 | 48 |
| Results: | | | | | | |
| - Overall degree of conversion of $C_2Cl_4$ (%) | 60.5 | 95.4 | 89.8 | 68.9 | 50.2 | 35.7 |
| - Selectivity (mol %) for: | | | | | | |
| F125 | 3 | 44.2 | 17 | 5.8 | 2.5 | 1.3 |
| F124 | 23.6 | 13.3 | 33.5 | 29.9 | 5.8 | 4.5 |
| F124a | 0.6 | 0.3 | 1.1 | 2.1 | 2 | 1.4 |
| F123 | 51.4 | 19.1 | 39.8 | 42.2 | 7.1 | 11.3 |
| F123a | 1.4 | 0.1 | 0.7 | 4.1 | 2.9 | 4.7 |
| F122 | 2.9 | 0.1 | 0.8 | 3.3 | 1.7 | 4.6 |
| F121 | 0 | 0 | 0 | 0 | traces | 0.1 |
| F133a | 0.7 | 7.2 | 2.3 | 2.4 | 21.1 | 17 |
| F115 | traces | 9.9 | 0.5 | 0.2 | 3.9 | 2.1 |
| F114 + F114a | 0.7 | 1.9 | 2.4 | 2.7 | 35 | 27.4 |
| F1111 | 14.4 | 1 | 1.7 | 6.7 | 10.9 | 18 |

Comparison of these results with those of Examples 1 and 2, carried out under substantially identical operating conditions, shows that:

catalyst C without chromium (Ex.3) is markedly less active (see $DC_0$ of $C_2Cl_4$) than the mixed Ni—Cr catalyst and, above all, less selective for F123+F124+F125;

catalyst D without nickel (Ex.4) has an initial activity that is comparable with that of the mixed Ni—Cr catalyst, but this activity is not stable with time and, furthermore, the selectivity for F123+F124+F125 is lower;

the catalyst E with a carbon support (Ex.5) has very low activity and very low selectivity.

Although the invention has been described in conjunction with specific embodiments, it is evident that many alternatives and variations will be apparent to those skilled in the art in light of the foregoing description.

We claim:

1. A continuous process of making compounds in the F120 series by catalytic fluorination comprising contacting in a gas phase perchloroethylene or pentachloroethane and HF with a catalyst consisting of nickel and chromium compounds in the form of oxides, halides and/or oxyhalides deposited on a support consisting of aluminum fluoride or of a mixture of aluminum fluoride and alumina, said nickel and chromium compounds being deposited on said support by impregnation; and wherein at least 90% of the conversion product is F123, F124 and F125;

wherein the weight content of nickel and chromium in the catalyst is between 0.5 and 20% in the case of each metal, the nickel/chromium atomic ratio being between 0.5 and 5;

wherein the reaction temperature is between 200 and 450° C.;

wherein the HF/$C_2Cl_4$ or $C_2HCl_5$ molar ratio is between 1/1 and 20/1; and wherein the contact time, calculated under the reaction conditions, is between 3 and 100 seconds.

2. Process according to claim 1, wherein the content is between 2 and 10% in the case of each metal.

3. Process according to claim 1, wherein the operating pressure is between 0 and 25 bars gauge.

4. Process according to claim 1, wherein the underfluorinated products are recycled to the reactor.

5. Process according to claim 1, wherein the operation is carried out in the presence of oxygen.

6. Process according to claim 1, wherein the nickel/chromium atomic ratio is about 1.

7. Process according to claim 1, wherein the reaction temperature is between 250 and 400° C.

8. Process according to claim 1, wherein said molar ratio is between 2/1 and 10/1.

9. Process according to claim 1, wherein contact time is between 5 and 30 seconds.

10. Process according to claim 9, wherein the contact time is between 7 and 20 seconds.

11. The process of claim 1 wherein at least 94% of said perchloroethylene or pentachloroethane is convertible to compounds in the F120 series.

12. The process of claim 1 wherein at least 95% of said perchloroethylene or pentachloroethane is convertible to compounds in the F120 series.

13. The process of claim 1 wherein at least 94% of said perchloroethylene or pentachlorethane is converted to compounds in the F120 series when the operating conditions are optimized.

14. The process of claim 1 wherein the reaction temperature is between 200 and 450° C., the operating pressure is between 0 and 25 bars gauge, and the contact time is between 3 and 100 seconds.

15. The process of claim 1 wherein impregnation includes:

(a) said support being combined with an aqueous solution of chromic acid ($CrO_3$) and a nickel salt, and said chromic acid being reduced; or (b) said support being combined with an aqueous solution of chromium and nickel salts.

16. The process of claim 15 wherein said chromic acid is reduced by inclusion of a reducing agent in the aqueous solution, or by thermal reduction.

* * * * *